United States Patent [19]
Netzer

[11] Patent Number: 5,880,320
[45] Date of Patent: Mar. 9, 1999

[54] COMBINATION PROCESS FOR MANUFACTURING ETHYLENE ETHYLBENZENE AND STYRENE

[76] Inventor: David Netzer, 1138 Hacienda Apt. 5, Los Angeles, Calif. 90069

[21] Appl. No.: 957,252

[22] Filed: Oct. 24, 1997

Related U.S. Application Data

[63] Continuation-in-part of Ser. No. 906,381, Aug. 5, 1997, abandoned.

[51] Int. Cl.$^6$ ............... C07C 2/64; C07C 4/02; C07C 7/04; C10G 7/02
[52] U.S. Cl. ............. 585/448; 585/323; 585/650; 585/809; 208/351; 203/DIG. 19
[58] Field of Search ............. 585/323, 448, 585/449, 650, 809; 208/351; 203/DIG. 19

[56] References Cited

U.S. PATENT DOCUMENTS

| | | | |
|---|---|---|---|
| 3,966,833 | 6/1976 | Cosyns et al. | 260/672 R |
| 4,009,217 | 2/1977 | Uitti | 260/669 R |
| 4,022,847 | 5/1977 | McClure | 260/683.68 |
| 4,107,224 | 8/1978 | Dwyer | 260/671 R |
| 4,496,784 | 1/1985 | Moorehead | 85/486 |
| 4,560,820 | 12/1985 | Field | 585/489 |
| 4,720,293 | 1/1988 | Rolles et al. | 62/24 |
| 5,463,154 | 10/1995 | Slim et al. | 585/261 |
| 5,675,054 | 10/1997 | Manley et al. | 585/809 |

OTHER PUBLICATIONS

Netzer, D., "Economically Recover Olefins From FCC Off-gases," *Hydrocarbon Processing*, pp. 83–91, Apr. 1997.

Primary Examiner—Glenn Caldarola
Assistant Examiner—Thuan D. Dang
Attorney, Agent, or Firm—Christie, Parker & Hale, LLP

[57] ABSTRACT

Gases and liquid products of the cracking zone of a ethylene production plant fractionated in a demethanizer to from a dilute ethylene stream containing about 5 to about 40 percent of the ethylene contained in the feed. The dilute ethylene is feed to an ethylbenzene plant and reacts with impure benzene. The product ethylbenzene is normally converted to styrene.

22 Claims, 5 Drawing Sheets

COMBINATION PROCESS FOR MANUFACTURING ETHYLENE ETHYLBENZENE AND STYRENE

CROSS REFERENCE TO RELATED APPLICATION

This is a continuation-in-part of application Ser. No. 08/906,381 filed Aug. 5, 1997 now abandoned.

FIELD OF INVENTION

The present invention is directed to an improved process of the production of ethylene for use in the production ethylbenzene and styrene.

BACKGROUND OF THE INVENTION

Conventional ethylene production consists of the following key process operation:

(a) Thermal cracking, in presence of dilution steam, of $C_2+$ hydrocarbon at about 15–25 psig and 1,500°–1,600° F. to form cracked gas containing ethylene in an amount of 25–40 wt % (and up to 80 wt % for net ethane feed), and other by products such as propylene, acetylene, hydrogen, methane and $C_3+$ products. The thermal section includes cracked gas cooling, steam generation and $C_9+$ hydrocarbon condensation. Traces of CO, $CO_2$ and $H_2S$ are formed in the cracking.

(b) Cracked gas compression to 400–600 psig, traces of $CO_2$ and $H_2S$ removal, drying, and bulk $C_4+$ product recovery by condensation at about 100° F., using cooling water.

(c) Acetylene conversion to ethylene via selective hydrogenation, chill down and cryogenic recovery of ethylene by fractionation at below −30° F.

(d) Recovery of propylene, propane and $C_4+$ hydrocarbons by warm distillation at above 80° F.

(e) Cascade refrigeration of ethylene and propylene refrigerants, to support the above, down to a temperature of below −100° F.

(f) Methane refrigeration and or expander to reach refrigeration below −180° F.

(g) In case of Naphtha feed, residual liquid products from cracking such as pyrolysis fuel oil and pyrolysis gasoline, which are rich in aromatics, are selectively hydrotreated for di-olefin and olefin saturation.

Efficient cryogenic recovery of the ethylene is a key element in design of ethylene plants. The motive power for compression and refrigeration, and consequently the capital cost escalates rapidly as the rate of ethylene recovery increases. For example, the typical ethylene recovery of 99.7–99.9% requires much higher investment and 50% more refrigeration energy in the demethanizer as compared with 95% rate of ethylene recovery. Thus, reduction of the marginal refrigeration required for ethylene recovery by using 95% or lower recovery could substantially improve the overall economics of the ethylene plant, if a down stream outlet, other than fuel gas, is found for the 5% more of the unrecovered gaseous ethylene. Normally the unrecovered ethylene 0.1–0.3% is routed with the methane to the fuel gas system. However, the value of ethylene as fuel is only about 15–20% of its equivalent value as downstream product. The ethylene product is commonly used as a feedstock to many downstream processing including ethylbenzene. Production of ethylbenzene from pure ethylene against dilute ethylene feed, although somewhat advantageous from a stand point of the ethylbenzene plant alone, is not an absolute requirement and its relative cost impact is rather marginal as compared with the estimated saving in the ethylene plant.

In recent years, processes for producing ethylbenzene from dilute ethylene feed streams have been developed by Badger, a subsidiary of Raytheon, ABB Lummus Global/CDTech, Sinopec and others. The key driving forces behind these new developments are the objectives of using offgases from fluid catalytic crackings (FCC) in petroleum refining. These offgases are at 150–250 psig and typically contain 8–18 vol % of ethylene, 3–9 vol %, of propylene and 12–20% hydrogen.

Limited integration of ethylbenzene and ethylene production was experienced in a number of locations including El Paso Products (Now Huntsman Chemical) in Odessa, Tex., where rich ethylene rich stream at 40 psig is compressed to 550 psig and feeds an ethylbenzene plant.

This invention combines the known technologies as developed for producing ethylbenzene from refinery FCC offgases, and for producing ethylene by conventional cracking of hydrocarbon feeds.

SUMMARY OF THE INVENTION

More particularly dilute ethylene at concentrations of about 3 to about 40 vol % and substantially free of propylene is extracted from a cryogenic demethanizer as an overhead gas. The bulk of the dilute ethylene stream comprises methane and hydrogen. The dilute ethylene stream at a typical pressure of about 330 to about 500 psig and after cold recovery and acetylene removal is the feed, along with common specification benzene, 99.9% wt % purity, or impure benzene, 95 to 98 wt % purity, to an ethylbenzene plant. The ethylbenzene is converted to styrene.

If styrene is produced on site along with the ethylbenzene, it normally is produced by thermal dehydrogenation of ethylbenzene. Steam at about 30 psig and 1,500 F. is used as a source of energy and also reduces the partial pressure of ethylbenzene, is directly premixed with ethylbenzene in a typical weight ratio of about 1.1 to about 1.8. Superheating of steam at about 30 to about 40 psig to about 1,500 F. in the cracking furnace of the ethylene plant becomes a second element of this invention. Low pressure saturated steam from the ethylbenzene and styrene plants and extraction steam from turbine drivers of the ethylene plant are superheated at the convection section of the cracker in the ethylene plant. The superheated steam is routed to the styrene plant, eliminating a specially dedicated superheater at the styrene plant.

If naphtha or heavier feeds are used, a pyrolysis gasoline product which is rich in benzene, is used as a source of benzene for the ethylbenzene plant. The benzene and co-boilers, cyclohexane and dimethylpentanes, are used as a feed to the ethylbenzene plant. The saturated $C_6$ co-boilers are purged from the ethylbenzene plant, ethylotion reaction loop.

DETAILED DESCRIPTION OF THE INVENTION

For illustration and process consistency, the invention will be described for an ethylene plant when naphtha is the sole feedstock followed by ethylbenzene production and subsequent production of styrene monomer. This enables demonstration of all the elements of the invention. This is reasonable since more than 50% of world ethylene production capacity originates from naphtha. The principles of this mode will be very similar for all other feedstocks.

The assumed capacity of the ethylene plant for consistency purposes is 1,000,000,000 lb/year, along with co-production of 400,000,000 lb/year of propylene and by products such as hydrogen, pyrolysis gasoline and pyrolysis fuel oil. About 8,300 hours per year of operation are assumed. Pyrolysis products such as ethane, propane, $C_4$ and $C_5$ are internally recycled and converted to ethylene and propylene. Acetylene is selectively hydrogenated to ethylene, and methylacetylene and propadiene are selectively hydrogenated to propylene.

According to the invention, for illustrative purposes about 15% of the crude ethylene originated in the cracking, is recovered as a dilute ethylene product at a concentration of about 10.0 vol. % and serves as a feed for production of 550,000,000 lb/year of ethylbenzene. The ethylbenzene is converted to 500,000,000 lb/year of styrene monomer, along with hydrogen and small amounts of other by products.

The cracking yield is based on of molecular weight of 92, a specific gravity of about 0.69, paraffin content of about 80 wt % (50% normal, 50% iso), naphtene content of about 10 wt % and aromatic content of 10 wt %. The naphtha contains less than 0.1 wt % olefins and traces of sulfur.

Figure 1:
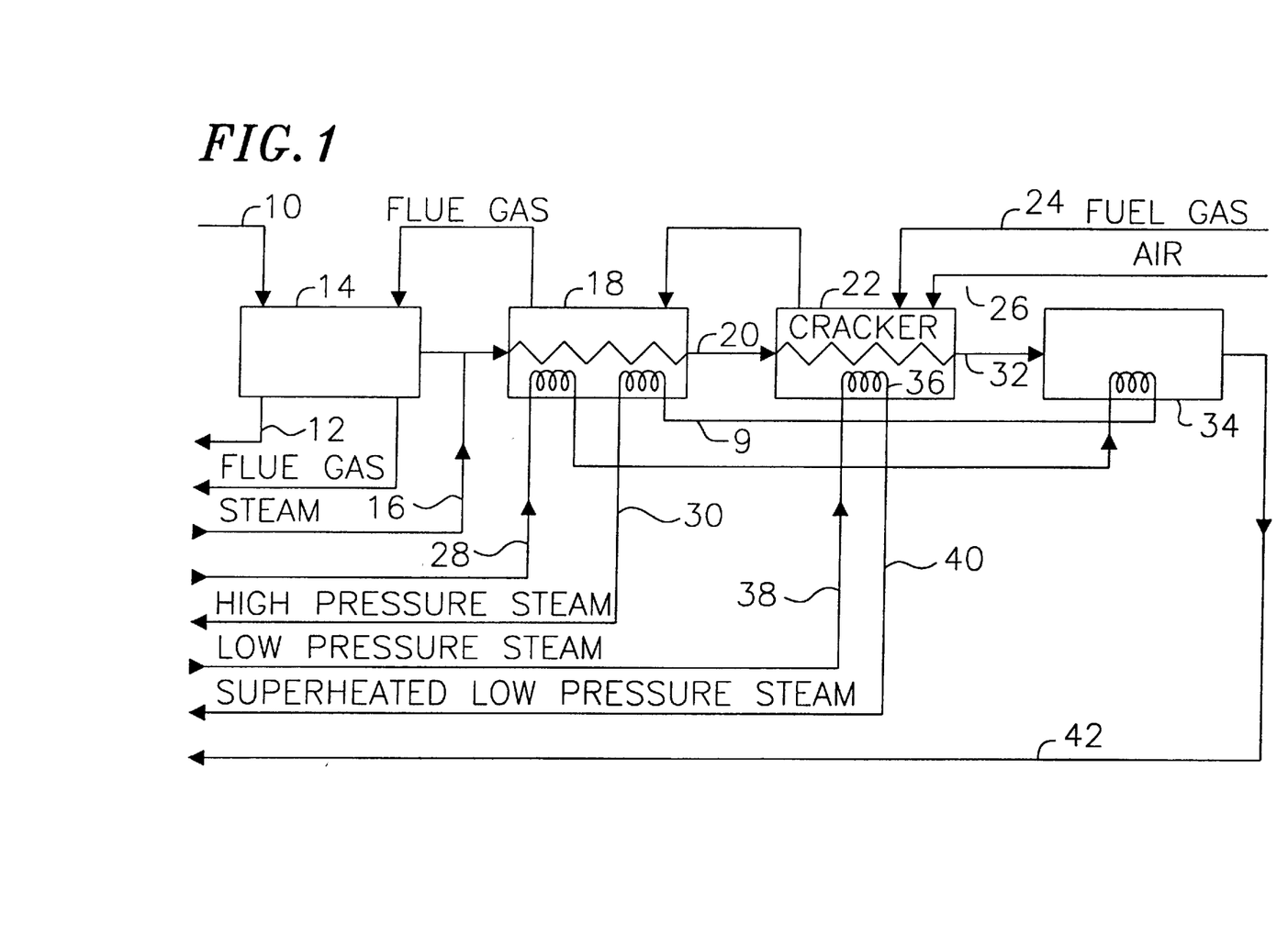
FIG. 1 illustrates the cracking section of the ethylene plant and heat recovery with high pressure steam generation and superheating and includes low pressure steam superheating for a styrene plant which is an element of the invention.

With reference now to FIG. 1, Naphtha net feed, 10 about 33,000 bpsd (331,000 lb/hr) and about 65,000 lb/hr of combined recycles 12 of $C_2H_6$ and $C_3H_8$ gas feed and $C_4H_{10}$, $C_5H_{12}$ and $C_6H_{14}$ liquids after hydrogenation, are vaporized in the vaporizer section of the furnace 14 and mixed with steam in line 16, at a typical weight ratio of about 0.5 steam to hydrocarbons feeds.

The steam helps reduce coking in the tubes of the furnaces, and also reduce the partial pressure of the hydrocarbons, thus increasing ethylene yield.

Figure 3:
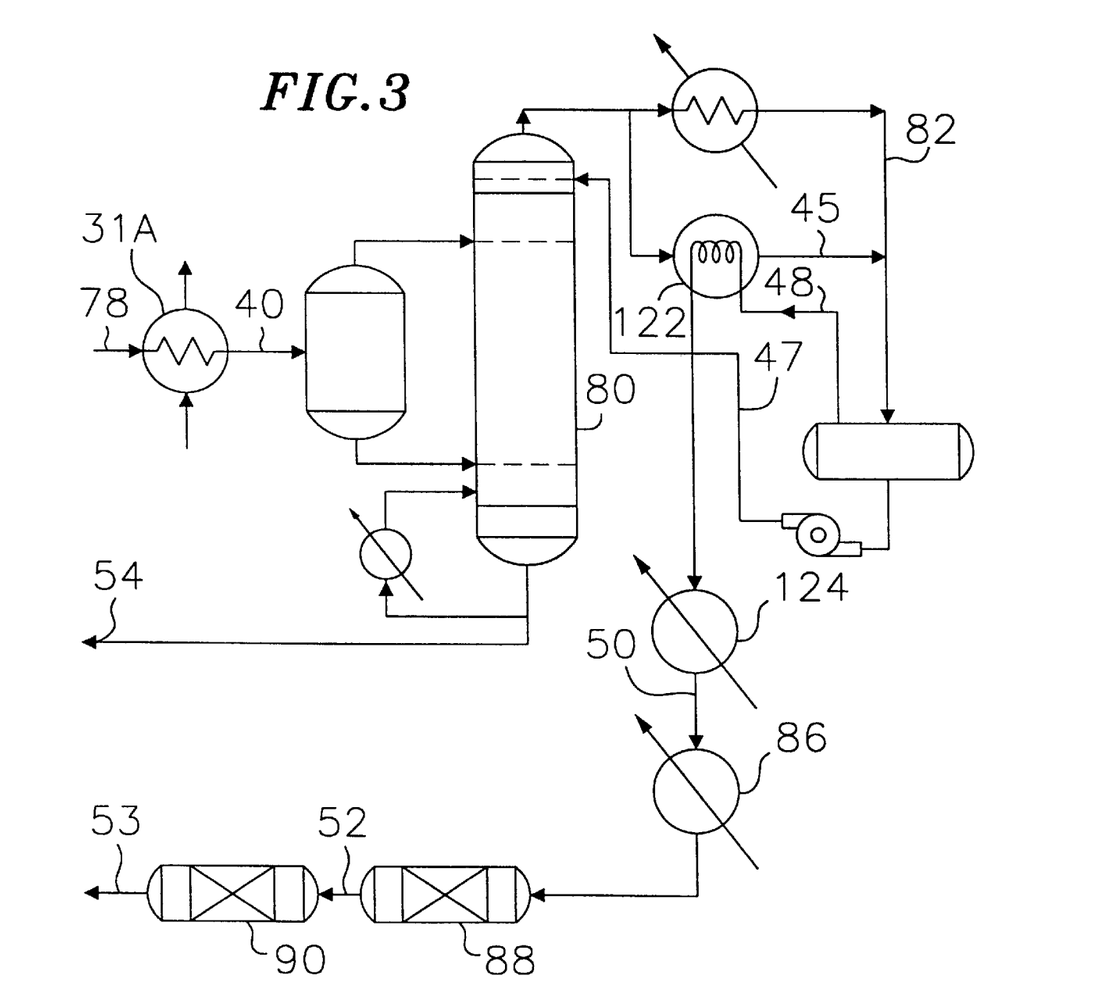
FIG. 3 illustrates the dilute ethylene recovery which is the key element of the invention.

This hydrocarbon steam mixture is further preheated in heater 18 and proceeds, line 20 prior to the cracking section of the pyrolysis furnace 22. The furnace is fired by fuel gas principally $CH_4$ product 24 as recovered from the down stream process. The source of the $CH_4$ with reference to FIG. 3, is the cryogenic separation zone (8) in the ethylene plant. However, its final recovery is from the vent gas scrubber 121 in the ethylbenzene plant FIG. 5. For the above naphtha net feed and the recycles, the following typical yield, in weight percent per pass, is shown in Table 1.

TABLE 1

| Component | Wt % | Destination |
|---|---|---|
| Hydrogen | 1.05 | Product to battery limit. |
| Methane | 15.8 | Fuel gas product to cracking furnaces |
| Acetylene | 0.9 | Converted to ethylene product |
| Ethylene | 29.6 | Main product to battery limits |
| Ethane | 6.2 | Recycled and converted to ethylene |
| Propadiene | 0.6 | Converted to propylene product |
| Propylene | 14.0 | Main product to battery limits |
| Propane | 0.4 | Recycled and converted to products. |
| $C_4$ Olefins + Paraffins | 9.5 | Hydrotreated and recycled to cracking |
| $C_5$ Olefins + Paraffins | 4.5 | Hydrotreated and recycled to cracking |
| Benzene | 6.5 | Light gasoline product, feed to ethylbenzene. |
| Toluene | 2.3 | Light gasoline product to battery limits or as a source of benzene |
| Xylene + Ethlybenzene | 0.4 | Heavy gasoline product to battery limits |
| Balance of Pyrolysis Fuel oil and pyrolysis gasoline ($C_6$–$C_9$) | 8.1 | Product to battery limit |
| $H_2S$ and $CO_2$ | | Traces waste to battery limits as sodium salts |
| CO | Trace | To fuel |

The net ethylene make is about 5.5 wt % of the naphtha feed in dilute form and about 29.0 wt % of the naphtha feed in concentrated pure form. The net propylene recovery is about 14.5 wt %.

In the heat recovery section 18 of the cracking furnace (cracker), hot combustion gas from the pyrolysis section undergoes heat recovery providing preheating boiler feed water 28 and superheating saturated steam 9 at about 1,900 psig and about 650 F. to about 1,800 psig and 980 F. stream 30. The cracked gas 32 is cooled in transfer line exchangers 34 to about 800 to about 840 F. by generating saturated steam at about 1,900 psig and about 650 F. The overall steam production is typically in balance as a motive power source for the cracked gas compression and refrigeration compression drivers of the ethylene plant.

Due to the process integration concept of the invention, an additional steam coil 36 is used to convert stream at a pressure of about 40 psig and below 450° F. 38 to provide steam at 1,500 F. for the styrene plant 40. For a styrene production rate of 500,000,000 lb/year, the thermal load of the 40 psig steam coils is estimated to be about 6% of the overall conventional fired duty in the cracking furnace (22).

Figure 2:
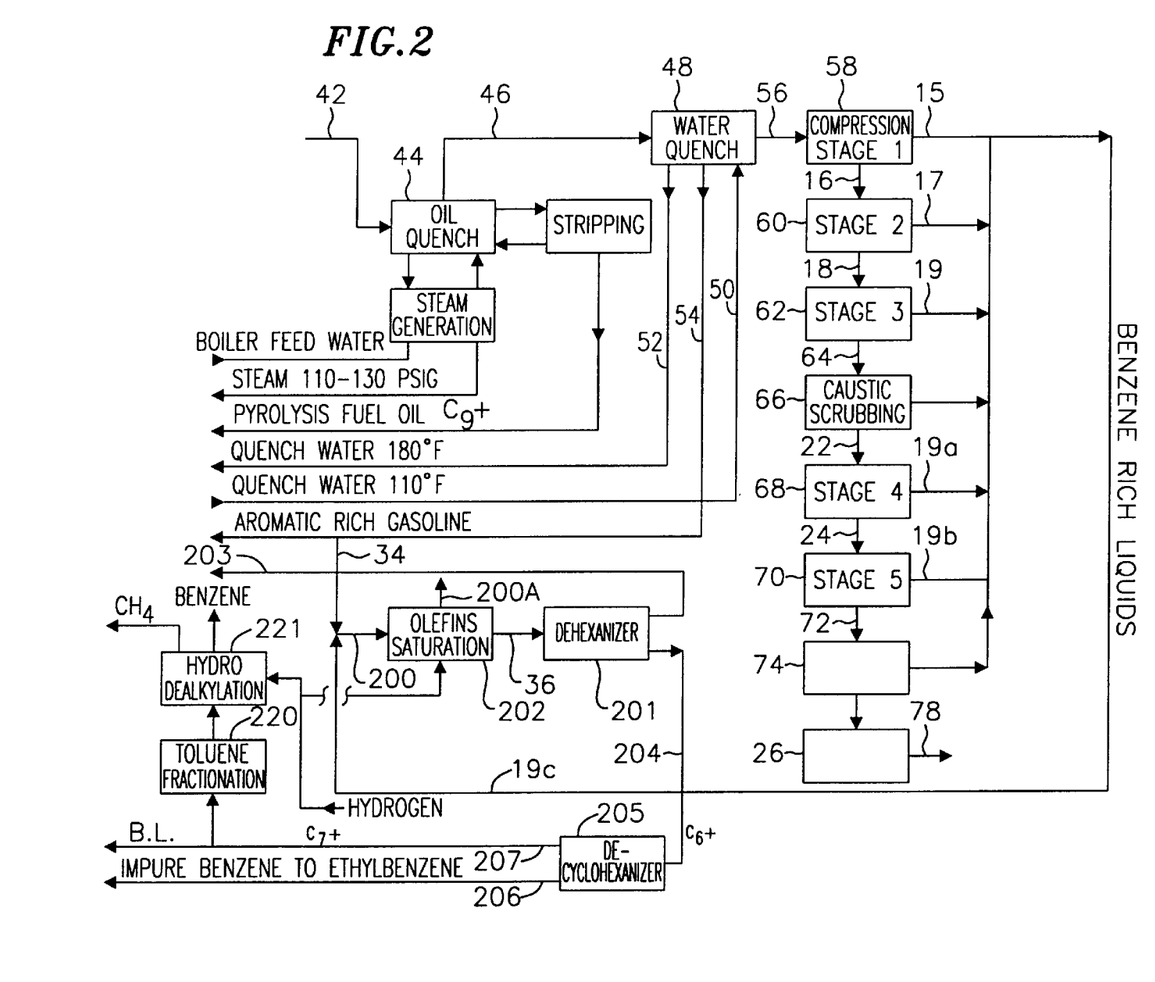
FIG. 2 illustrates the quench oil and quench water pyrolysis gasoline and pyrolysis fuel oil recovery, cracked gas compression, $CO_2$ and $H_2S$ removal, cracked gas drying, pyrolysis gasoline hydrotreating, dehexanizer, benzene recovery, toluene conversion to benzene as a feed to the ethylbenzene plant.

With reference to FIG. 2 The cracked gas at about 800 to about 840° F. and 10 psig in line 42 after steam generation is quenched with pyrolysis fuel oil in quench zone 44 using oil recycle and heat absorption by generating saturated steam at 110–130 psig.

The net product made after stripping of light pyrolysis products is $C_9$+, pyrolysis fuel oil. The steam at 110–130 psig is ultimately used as a dilution steam for the naphtha and recycle feeds 16. Overhead gas 46 from the quench oil system at about 220–250 F. proceeds to the quench water system 48, and preheat quench water at 110° F. in 50° to 180° F. in line 52 and recovery of aromatic rich $C_6$–$C_9$ pyrolysis gasoline 54. The 180° F. water 52 serves as a low level heat source to a number of reboiling services in the plant facility. After utilization of the low level heat, water at about 110° F. is recycled back to the quench water system 48.

Quenched gas is further cooled to about 100° F. with about 88° F. cooling water (depending on ambient conditions) and the bulk of the water vapors and the $C_6+$ products are condensed and separated. The cracked gas at about 5.0 psig proceeds by line 56 to compression. The gas is compressed to about 400–600 psig in four to five stages. For illustration purposes five stages of compression to about 520 psig are assumed. After three stages of compression (58, 60, and 62) to about 140 psig, the gas 64 proceeds to caustic scrubber (66) for $CO_2$ and $H_2S$ removal and further compressed at 68 and 70 to about 520 psig in line 72 and aftercooled to about 100° F. The gas is further cooled in exchanger 74 to about 60° F. by refrigeration or cold recovery prior to water/hydrocarbon separation. The gas proceeds to molecular sieve dryer 26 as needed for downstream cryogenic product recovery. At this point about 99% of the benzene and $C_6$, 85% of the $C_5$ hydrocarbon and 65% of the $C_4$ hydrocarbons are condensed and separated in lines at 15, 17, 19, 19A and 19B and send to raw pyrolysis gasoline 34.

Water and hydrocarbon liquids, mostly $C_4$, $C_5$, and $C_6$ are condensed in the interstage and after stage cooling of the cracked gas compression FIG. 2, stream 15, 17, 19, 19A and also from dryer prechilling (74) and water is separated (not shown). The combined hydrocarbon liquid 19c combines with aromatic rich stream 34 to feed stream 200 to selective olefin and di-olefin saturation unit 202. The hydro treated stream 36 free of sulfur, proceed to dehexanizer (201) where all $C_4$, $C_5$, and all $C_6$ except cyclohexane and benzene are separated overhead, at an atmospheric cut point of 167° F. This light saturated liquid 200 A recycles back to(cracking) vaporizer section of the cracking furnace 14, (FIG. 1).

Figure 5:
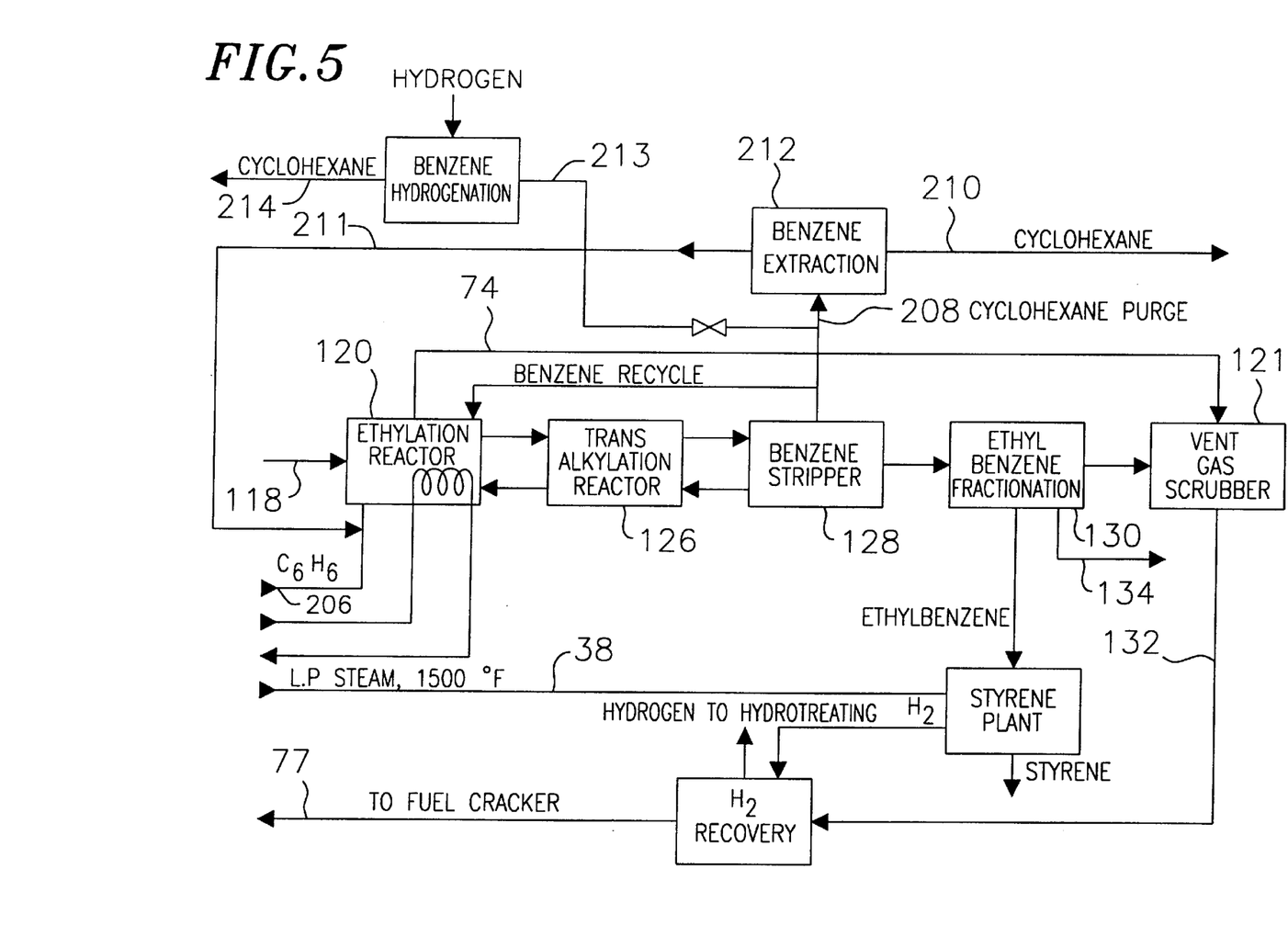
FIG. 5 illustrate ethylbenzene and styrene production along with hydrogen recovery.

Bottom product from 201 fractionation, proceeds to de-cyclohexanizer 205 where benzene, cyclohexane and dimethylpentanes are separated, at an atmospheric cut point of 183° F. The overhead product, stream 206 is impure benzene containing typically 2–8 wt % of cyclohexane and dimethylpentanes. This impure benzene is used as a feed for the ethylbenzene 120 (FIG. 5). Toluene rich stream 207, can proceed to battery limits or alternately to toluene fractionation 220. Overhead toluene proceeds to conventional hydro-dealkylation 221 where hydrogen reacts with toluene to form benzene and methane.

With reference to new FIG. 3, about 12710 lb-mol/hr of dry cracked gas at about 500 psig and about 60° F. in line 78 with the molecular composition shown in Table 2, proceeds to a chill down train for cryogenic product recovery.

TABLE 2

| Component | Mol % |
|---|---|
| Hydrogen | 16.9 |
| Methane | 31.8 |
| Acetylene | 0.85 |
| Ethylene | 33.0 |
| Ethane | 5.65 |
| CO | 0.25 |
| Propadiene/ Methyl Acetylene | 0.35 |
| Propylene | 8.90 |
| Propane | 0.45 |
| $C_4$ olefins | 1.40 |
| Butanes | 0.15 |
| $C_5+$ | 0.25 |

In an alternate design (not shown) cracked gas after the 4 stages of compression, at about 270 psig, will go through $H_2O/CO_2$ removal, molecular sieve drying and than a chill down for $C_2/C_3$ separation in a front end deethanizer. The $C_2$ and lighter fractions are warmed up undergo acetylene hydrogenation to form ethylene and the $C_3$ and heavier hydrocarbon liquids proceed to propylene and $C_4+$ recovery. The acetylene free light gas at about 260 psig is further compressed through the 5th stage to about 520 psig. In yet another alternate design (not shown) the front end separation of the $C_2$ and lighter hydrocarbons will be carried out at about 500 psig using double fractionation system.

In the primary design, as well as alternate designs, the dry cracked gas at about 500 psig and about 60° F. in line 78 is chilled down to about −200° F. using propylene and ethylene refrigeration, followed by an expander or methane refrigeration (not shown). At this point essentially all the ethylene (99.9%) is condensed in several stages along with the bulk of the methane, and hydrogen rich gas (75% $H_2$) is separated from the crude ethylene liquids which are fed to a demethanizer 80, operating at about 70 to about 550 psig, more preferably at about 300 to about 500 psig and, for this illustration, preferably about 460 psig. In a conventional design, the overhead product of the demethanizer overhead is essentially methane, some residual hydrogen with very minimal quantity, say 100 vol. ppm, of ethylene. The bottom product 54 is essentially ethylene, ethane, propylene and $C_3+$ hydrocarbons. Methane content is under 100 ppm and hydrogen content is essentially nil. In a conventional design, the ethylene in the overhead of the demethanizer at 48 represents a net ethylene product loss to the fuel gas system, thus a good economical design should minimize its content by appropriate reflux of liquid methane stream 47 at typically about −145° F. The cold for the reflux is provided by ethylene refrigeration at about −150° F. which corresponds to slightly above its atmospheric pressure. Typically 99.8% of the ethylene, and essentially 100% of the ethane and acetylene from the charge gas are recovered as a bottom product for further processing and separation. The same is essentially true for the alternate designs except that essentially no $C_3+$ and acetylene are present in the bottom of the demethanizer. In some conventional designs, the pressure of the demethanizer is let down to about 70 psig.

In the conventional design stream 48 the $CH_4/H_2$ overhead from the demethanizer at about 460 psig is typically expanding to fuel gas pressure of about 50 psig in a turbo-expander, (not shown) generating motive power as well as refrigeration (needed for the low temperature ethylene condensation and hydrogen separation). The cold is recovered from the $H_2/CH_4$ rich gas prior to diversion to the fuel system for subsequent combustion in the cracking furnaces.

Figure 4:
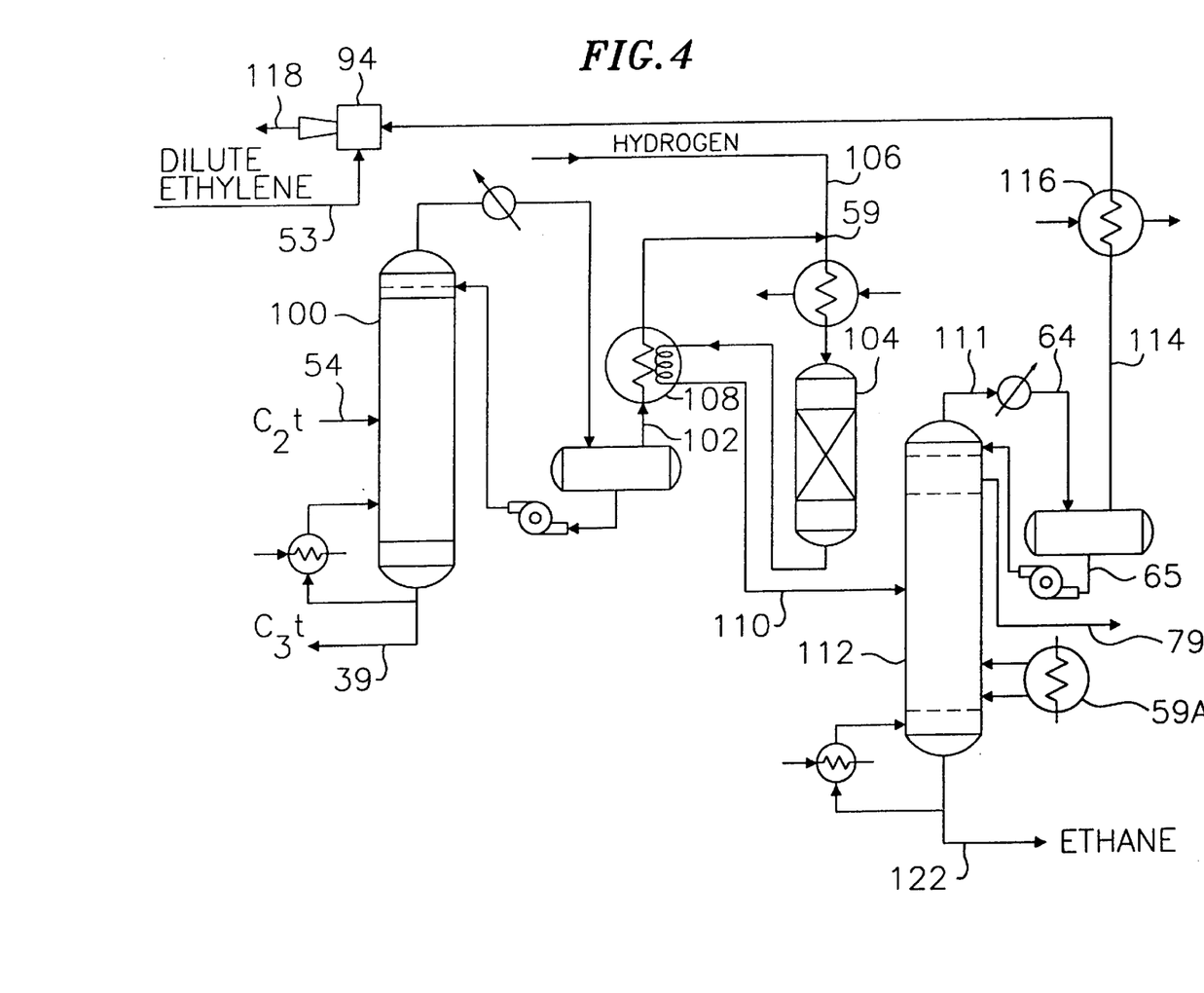
FIG. 4 illustrates the ethylene recovery, acetylene reactor and off specification ethylene diversion to the ethylbenzene plant, which is an element of the invention.

In the instant invention all hydrogen separation occurs in the demethanizer, unless the invention is applied toward revamp of an existing plant. The bottom liquid product 54 of the demethanizer 80 at about 50° F. proceeds is let down to deethanizer 100 operating at about 280 psig. The ethylene, acetylene and ethane are separated as overhead product 102 and propylene and $C_3+$ hydrocarbons as bottom products 39. The overhead product 102 with about 1.9 wt % acetylene is reheated to 130° F. and to passed acetylene hydrogenator 104 with outside hydrogen source 106. The acetylene free, $C_2$ vapor is condensed by preheating the feed in exchange 108 and proceeds to ethylene fractionator 112 at about 240 psig, or lower pressure depending on final disposition of the ethylene product, and the refrigeration system. The above acetylene removal step is not required for the alternate designs, since acetylene is converted upstream of the demethanizer.

The overhead product 114 from the ethylene fractionator 112 is off specification ethylene product. The side draw 79 typically drawn about 8–10 trays below the top in the ethylene fractionator. Residual methane originated from the demethanizer and excess hydrogen from the acetylene converter, are vented (if necessary) from the overhead as off specification ethylene 114.

The off specification ethylene is suitable as a feed to the ethylbenzene plant. The amount of flow after cold recovery in 116 is small. The ethylene is mixed in an ejector 94 with the bulk of the dilute ethylene feed 53 containing about 10% ethylene and about 5 ppm acetylene and propylene, and send to ethylbenzene plant 120. The bottom product 122, essentially ethane is re-vaporize via cold recovery and sent to the cracking section 14. In the alternate design (not shown), demethanizer bottom proceeds directly to the ethylene fractionator 112. The $C_3+$ hydrocarbon product undergoes separation of $C_3$ and $C_4+$ hydrocarbon (not shown). The $C_3$ product is undergoes hydrogenation of the methyl acetylene and propadiene and proceeds to propylene fractionation (not shown). The overhead product is propylene, the bottom product is propane which is recycled to the cracking section 14.

In the invention the demethanizer is operating in a "sloppy cut" mode, for ethylene and also separate all the hydrogen at the overhead. For illustrative purposes the demethanizer overhead rather than operating with full ethylene recovery at the bottom and essentially no ethylene at the top, has 10 mol % or more ethylene in the overhead and typical propylene content of below 5 ppm by volume. The methane specification for the bottom will be about 100 to about 2,000 mol-ppm. By allowing ethylene to escape from the top, at 10 mol % concentration, about 15% of the ethylene, about 2% of the ethane, and about 8% of the acetylene feeds to the demethanizer, will go overhead. The overhead product gas about 6,890 lb-mol/hr at about –115° F. and about 450 psig will have the approximate molecular composition shown in Table 3:

TABLE 3

| Component | Lb-mol/hr | Mol % |
| --- | --- | --- |
| Hydrogen | 2147 | 31.1 |
| CO | 31 | 0.44 |
| Methane | 4041 | 58.6 |
| Acetylene | 9 | 0.13 |
| Ethylene | 650 | 9.5 |
| Ethane | 13 | 0.19 |
| Propylene | 0.03 | 5 ppm |

With the reference to FIG. 3, the gas is preheated via cold recovery 122 and 124 to about 92° F. and further preheated in exchanger 86 to 130° F. prior to acetylene reactor 88. The acetylene free gas 52 proceeds to activated carbon beds 90 for removal of $C_6$–$C_8$ trace formed in acetylene reactor 88. For the alternate case, these steps are not required. As further optimization, not shown, side reboiler and side condensers can be used for increasing refrigeration economy. Dilute ethylene can be made as a side draw product.

Propylene and acetylene free gas at about 415 psig in line 53 combines with off specification ethylene from ethylene fractionator in ejector 94 and the combined gas 118 proceeds as feed to the ethylation reactor section 120 of the ethylbenzene plant.

For process control purposes, liquid ethylene product provides up to 10% of the feed to the ethylbenzene plant.

Liquids, mostly $C_4$, $C_5$, and $C_6$ as condensed in the gas compression inter and after coolers FIG. 2. 19C combines with 34 to a $C_4$–$C_8$ raw pyrolysis gasoline 200. The raw pyrolysis gasoline is undergoing selective di-olefins and olefins saturation qt. 201. Hydrotreated liquid 36 and $C_6$ boilers below benzene (170° F.) are separated at 202, and sent at 203 for cracking at 14. $C_6+$ stream at 204, is sent to de-cyclohexanizer 205 where benzene and cyclohexane are separated. The benzene cyclohexane, 206 containing over 90 wt % benzene is used as impure benzene feed to the ethylbenzene plant 120.

In the ethylbenzene plant 120, ethylene reacts with benzene feed 206 and stoichiometric excess of benzene. The exothermic reaction forms ethylbenzene and poly ethylated benzene (PEB). In a separate trans alkylation reactor 126 the polyethylated benzene reacts with benzene to form ethylbenzene. After series of products fractionation and purifications (128–130), the final products are: (1) Ethylbenzene with purity above 99.5%; (2) Vent gas 132 depleted of 95–99% of the ethylene feed and containing 34.5 mol % of hydrogen; and (3) A small amount, about 0.5–2.0%, of the benzene remains converted to polyethylated product commonly referred to as flux oil (134). The flux oil is routed to pyrolysis fuel oil. The cyclohexane and dimethylpentanes are close boilers to benzene and purged 208 from the benzene recycle loop with 75 wt % benzene. The purge will go to battery limits or to conventional extraction of benzene 212 and benzene 211 will recycle to the feed. The cyclohexane residue 210 will go to battery limits. Additional benzene can be made by separation of toluene. FIG. 2, 220 and conversion of toluene to benzene by hydrodelakylation 221 which is a conventional and known process. After toluene conversion, the benzene, will be used as make up about 60% of the requirement for the ethylbenzene production. Without toluene conversion, the benzene will provide about 40% of the requirement. As an alternative, cyclohexane rich purge 213 will go to benzene hydrogenation for cyclohexane production 214.

If high benzene conversion yield is desired, the cyclohexane rich purge 208 can be ethylated in a purge reactor (not shown). The benzene reacts with ethylene to form ethylbenzene and polyethylated benzene. The reaction products will go through a fractionation (not shown). Benzene cyclohexane and other co-boilers will be separated at an atmospheric cut point of about 183° F. Ethylbenzene and polyethylated benzene will be recycled to the trans alkylation reaction 126 (FIG. 5).

As another alternative (not shown) cyclohexane can be selectively oxidized to cyclohexanol. The cyclohexanol will be separated by fractionation to be recovered as valuable product.

I claim:

1. A process for the simultaneous coproduction of ethylbenzene from dilute ethylene along with pure ethylene as a key product which comprises:

a) forming in one or more hydrocarbon cracking zones a cracked gas comprising hydrogen, carbon monoxide, methane, acetylene, ethylene ethane and propylene and a cracked liquid which includes pyrolysis gasoline comprising benzene, toluene and cyclohexane;

b) fractionating said cracked gas in a demethanization zone to form (1) a dilute ethylene vapor mixture comprising hydrogen, carbon monoxide, methane, ethylene and no more than 200 mol-ppm of propylene in which ethylene is present in an amount of from about 3 to about 35 percent of the ethylene fed to said demethanization zone at a pressure of from about 70 to about 550 psig, whereby the dilute ethylene vapor mixture undergoes no further phase change, and (2) bottoms comprising ethylene and ethane;

c) reheating the dilute ethylene vapor mixture;

d) feeding the dilute ethylene vapor mixture to an ethylbenzene production zone;

e) providing a benzene feed comprising benzene;

f) introducing the benzene feed to the ethylbenzene production zone;

g) reacting the ethylene in the dilute ethylene feed with the benzene in the benzene feed to form ethylbenzene in the ethylbenzene production zone; and h) further purifying the bottoms for ethylene product recovery.

2. A process as claimed in claim 1 wherein the dilute ethylene vapor mixture further comprises acetylene and wherein the acetylene is hydrogenated to ethylene prior to being fed to the ethylbenzene production zone.

3. A process as claimed in claim 1 in which the demethanization zone is operated at a pressure from 330 to about 550 psig.

4. A process as claimed in claim 1 in which the dilute ethylene vapor mixture contains from about 5 to about 40 mol percent ethylene.

5. A process as claimed in claim 1 in which essentially all of the hydrogen in the cracked gas is separated with the dilute ethylene vapor mixture at a temperature above about −150° F. and at pressures of about 300 to about 550 psig.

6. A process s claimed in claim 1 in which the dilute ethylene vapor mixture contains from about 8 to about 25 mol percent ethylene.

7. A process as claimed in claim 1, wherein the methane content of bottoms contains up to about 2000 mol-ppm of methane and wherein the process further comprises (1) feeding the bottoms to an ethylene fractionation zone to form an off specification, methane and hydrogen rich ethylene overhead stream containing at least about 92 mol % ethylene and a concentrated ethylene side stream containing above about 99.5 mol % ethylene, (2) combining said methane and hydrogen rich off specification ethylene overhead stream with the at least a portion of the dilute ethylene overhead vapor mixture in an injection compression zone to form a compressed mixture and (3) feeding the compressed mixture to the ethylbenzene production zone.

8. A process as claimed in claim 7 in which the concentrated ethylene side stream from the ethylene fractionation zone provides up to 10 percent of the feed to the ethylbenzene production zone.

9. A process as claimed in claim 1 further comprising producing steam in the ethylbenzene production zone, superheating the steam at 10 to 70 psig in the cracking zone and feeding the steam to a styrene production zone as a source of thermal energy during conversion of ethylbenzene to styrene.

10. A process as claimed in claim 9 in which the steam is superheated to about 1200° to about 1650° F. at about 20 to about 40 psig.

11. A process as claimed in claim 9 in which the steam is extracted from a steam turbine of a refrigeration compressor.

12. A process as claimed in claim 11 in which the stream is provided at a pressure from about 30 to about 70 psig from a reaction zone of said ethylbenzene formation zone and waste heat recovery of said styrene formation zone.

13. A process as claimed in claim 1 further comprising converting toluene contained in the pyrolysis gasoline to benzene by hydrodealkylation and feeding the benzene formed to the ethylbenzene production zone.

14. A process as claimed in claim 1 further comprising purging a cyclohexane rich stream from the ethylbenzene production zone and passing the stream to a benzene hydrogenation zone for production of cyclohexane.

15. A process as claimed in claim 1, wherein the benzene feed comprises about 1.0 to 20.0 wt % cyclohexane and dimethylpentanes.

16. A process as claimed in claim 15 further comprising purging a benzene stream comprising about 7.0 to 60 wt % cyclohexane and dimethylpentanes out of the ethylbenzene production zone.

17. A process as claimed in claim 16 in which the purged stream proceeds to a purge reactor where benzene reacts with ethylene to form ethylbenzene and polyethylated benzene.

18. A process as claimed in claim 1, wherein the benzene feed comprises about 3.0 to 8.0 wt % cyclohexane and dimethylpentanes.

19. A process as claimed in claim 18 further comprising purging a benzene stream comprising about 10 to 30 wt % cyclohexane and dimethylpentanes out of the ethylbenzene production zone.

20. A process as claimed in claim 19 in which the purged stream proceeds to a purge reactor where benzene reacts with ethylene to from ethylbenzene and polyethylated benzene.

21. A process as claimed in claim 1, wherein the benzene feed and the dilute ethylene are originate from different hydrocarbon cracking zones.

22. A process as claimed in claim 1, further comprising converting the ethylbenzene produced to styrene.

* * * * *

UNITED STATES PATENT AND TRADEMARK OFFICE
CERTIFICATE OF CORRECTION

PATENT NO.   : 5,880,320
DATED        : March 9, 1999
INVENTOR(S)  : David Netzer

It is certified that error appears in the above-identified patent and that said Letters Patent is hereby corrected as shown below:

Column 9,
Line 29, replace "process s" with -- process as --.

Column 10,
Line 10, replace "stream" with -- steam --.

Signed and Sealed this

Twenty-fifth Day of March, 2003

JAMES E. ROGAN
*Director of the United States Patent and Trademark Office*